US005417104A

United States Patent [19]

Wong

[11] Patent Number: 5,417,104
[45] Date of Patent: May 23, 1995

[54] DETERMINATION OF PERMEABILITY OF POROUS MEDIA BY STREAMING POTENTIAL AND ELECTRO-OSMOTIC COEFFICIENTS

[75] Inventor: Po-zen Wong, Amherst, Mass.

[73] Assignee: Gas Research Institute, Chicago, Ill.

[21] Appl. No.: 68,967

[22] Filed: May 28, 1993

[51] Int. Cl.⁶ .................. E21B 49/00; G01V 3/18; G01N 15/08
[52] U.S. Cl. .................. 73/38; 324/353; 324/347
[58] Field of Search .......... 73/38; 324/353, 348, 324/347, 355, 352, 351

[56] References Cited

U.S. PATENT DOCUMENTS

| | | | |
|---|---|---|---|
| 2,433,746 | 12/1947 | Doll | 324/353 |
| 2,550,005 | 4/1951 | Doll | 324/353 |
| 2,592,125 | 4/1952 | Doll | 324/351 |
| 2,713,146 | 7/1955 | Doll | 324/351 |
| 2,814,017 | 11/1957 | Doll | 324/353 |
| 2,974,273 | 3/1961 | Vogel et al. | 324/353 |
| 3,243,695 | 3/1966 | Roark et al. | 324/376 |
| 3,302,101 | 1/1967 | Glanville | 324/376 |
| 3,599,084 | 8/1971 | Bakamjian | 324/353 |
| 3,599,085 | 8/1971 | Semmelink | 324/386 |
| 3,638,106 | 1/1972 | Cram | 324/351 |
| 3,691,456 | 9/1972 | Warren et al. | 324/351 |
| 4,427,944 | 1/1984 | Chandler | 324/523 |
| 4,573,342 | 3/1986 | Jones | 73/38 |
| 4,626,773 | 12/1986 | Kroeger et al. | 324/642 |
| 4,671,100 | 6/1987 | Doussiet | 73/38 |
| 4,686,477 | 8/1987 | Givens et al. | 324/366 |
| 4,730,162 | 3/1988 | Vinegar et al. | 324/362 |
| 4,769,606 | 9/1988 | Vinegar et al. | 324/366 |
| 4,791,822 | 12/1988 | Penny | 73/38 |
| 4,864,845 | 9/1989 | Chandler et al. | 73/38 |
| 4,868,751 | 9/1989 | Dogru et al. | 364/422 |
| 4,876,512 | 10/1989 | Kroeger et al. | 324/376 |
| 4,922,758 | 5/1990 | Penny | 73/38 |
| 4,961,343 | 10/1990 | Boone | 73/152 |
| 4,979,393 | 12/1990 | Leung et al. | 73/155 |
| 5,010,301 | 4/1991 | Leung et al. | 324/376 |
| 5,237,854 | 8/1993 | Jones | 73/38 |
| 5,269,180 | 12/1993 | Dave et al. | 73/38 |

FOREIGN PATENT DOCUMENTS 0043768 1/1982 European Pat. Off. .

OTHER PUBLICATIONS

The Leading Edge, Dec. 1993, pp. 1169–1173, A. H. Thompson et al., "Geophysical applications of electrokinetic conversion".

Primary Examiner—Hebron E. Williams
Assistant Examiner—J. David Wiggins
Attorney, Agent, or Firm—Speckman, Pauley & Fejer

[57] ABSTRACT

Process and apparatus for determination of permeability of porous media by measurement at finite frequency of streaming potential and electro-osmotic induced voltage and pressure due to applied finite frequency pressure oscillations and alternating current, respectively. The inter-electrode distance between points of application and measurement of the alternating signals at a finite frequency is small compared to the wavelength of the pressure oscillations and alternating current voltage.

47 Claims, 8 Drawing Sheets

DETERMINATION OF PERMEABILITY OF POROUS MEDIA BY STREAMING POTENTIAL AND ELECTRO-OSMOTIC COEFFICIENTS

BACKGROUND OF THE INVENTION

1. Field of the Invention

This invention relates to a process and apparatus for determination of permeability of porous media, such as underground formations, especially those having low permeability of shaley formations. Permeability is determined according to this invention by measurement at a finite frequency of streaming potential and electro-osmotic induced pressure due to applied finite frequency pressure oscillations and alternating current, respectively, with use of both measurement coefficients in conjunction with electrical conductivity, which may be measured simultaneously or separately, to obtain the formation permeability. In the apparatus of this invention, the differential pressure and induced voltage is measured at substantially the point where pressure oscillations and alternating current are applied, that is, the distance between application and measurement electrodes is small compared to the sonic or subsonic wave length and the electrodes are removed from formation fluid flow paths.

2. Description of Related Art

Several prior patents teach application of pulsed pressure and measurement of an a.c. signal of defined frequency in the measurement of streaming potential in a porous underground formation: U.S. Pat. No. 2,433,746 teaches vigorous vibration of a down hole apparatus to generate pressure oscillations for measurement, with one electrode down the borehole and the other at the surface, of the potential to ascertain the streaming potential: U.S. Pat. No. 2,550,005 teaches a modification of the method taught by the U.S. Pat. No. 2,433,746 by pressurizing the entire well to produce the periodic pulses in the borehole liquid; and U.S. Pat. No. 3,599,085 teaches use of a sonic transducer periodically exciting a formation at low frequencies to cause periodic electrokinetic potentials which are measured at a location near the transducer and at a location spaced from the transducer, the ratio of the measured potentials being related to the electrokinetic skin depth to provide an indication of permeability of the formation. U.S. Pat. No. 4,427,944 teaches application of pressure of alternating polarity to the formation and measurement of the generated transient streaming potentials in the time domain to estimate the characteristic response time which is inversely proportional to the formation permeability.

U.S. Pat. No. 2,814,017 teaches measurement of the difference in phase between periodic pressure waves passed through a formation and potentials generated by the oscillatory motion of the formation caused by these pressure waves and, conversely, application of a periodically varying electric current to the formulation fluid to generate periodic pressure waves in the formation by electro-osmosis. Measurements of the phase shift in the frequency domain between the generating and generated quantities is said to be a measure of permeability of the formation. U.S. Pat. No. 4,730,162 teaches time domain induced polarization with a square wave of alternating polarity being applied intermittently and alternately for induced polarization logging.

U.S. Pat. No. 3,302,101 teaches measurement of electroresistivity of a core sample maintained under constant pressure with power supplied by an alternating current and U.S. Pat. No. 4,686,477 teaches application of multi-frequency electric current to a sub-surface formation for ascertainment of the relation of resistivity versus frequency for characterization of rock lithology.

The methods taught by the prior art patents have many disadvantages. Neither the streaming potential nor the electro-osmotic measurement alone is a reliable indication of formation permeability, especially in formations of low permeability. Attempts to measure the streaming potential signal with electrodes at distances greater than one wavelength from each other are flawed since pressure oscillation propagates as a sound wave and the pressure difference would depend on both the magnitude and the phase of the wave and the streaming potential signal would be very low since considerable energy is lost to viscous dissipation over such a distance. Movement of the electrode in well fluid is disadvantageous since its own surface potential would be disturbed and oscillate at the same frequency causing an oscillating voltage much stronger than the streaming potential signal. Application of a d.c. flow to a formation and measurement of the response voltage in the time domain will not work in low permeability formations since the longer response time and very low streaming potential signal is dominated over by drifts of the electrodes' interfacial voltage over time. Measurement of a pressure signal resulting from the electro-osmotic effect would be even more difficult since it would be very weak and inseparable from the much larger voltage signal at the same frequency resulting from formation resistivity. Proposed measurement of the phase-shift in the frequency domain would be even more difficult than the suggested measurement of the response time in the time domain.

SUMMARY OF THE INVENTION

It is an object of this invention to overcome many of the disadvantages of prior art streaming potential and electro-osmotic pressure measurements.

It is another object of this invention to provide a method of utilizing both streaming potential and electro-osmotic coefficients in conjunction with conductivity (resistivity) to determine permeability of porous formations.

It is yet another object of this invention to provide a method for determination of permeability of porous media which is effective for low permeability shaley formations.

Another object of this invention is to provide apparatus suitable for ascertainment by a single instrument of streaming potential and electro-osmotic coefficients and rock conductivity by both sub-surface formation measurements and by laboratory core sample measurements.

In estimating reserves and in predicting producibility from both gas and oil underground deposits, it is important to know the permeability and physical parameters of rock formations. Streaming potential and electro-osmosis are known electrokinetic phenomena which result from the presence of surface charge in porous media and represent the coupling between fluid flow and electric current flow in such media. According to the present invention, a.c. measurement at the finite frequency of streaming potential and electro-osmotic induced voltage and pressure, respectively, results in coefficients $K_1$ and $K_2$, respectively, from which the zeta-potential ($\zeta$) which affects the surface conductivity and the throat size (R) which affects hydraulic permeability can be calculated. These parameters, $\zeta$ and R, may be used in interpretation methods to obtain the formation factor (F) and the permeability (k).

Streaming Potential Coefficient $K_1$ is obtained by a.c. measurement of streaming potential voltage induced by applied pressure oscillations at a finite frequency, as will be described in greater detail, by the relation:

$$K_1 = V_s/P_a \qquad \text{Eq. 1}$$

wherein $V_s$ is the measured induced streaming potential voltage and $P_a$ is the applied pressure.

Electro-osmotic Coefficient $K_2$ is obtained by a.c. measurement of electro-osmotic pressure and applied voltage, as will be described in greater detail, by the relation:

$$K_2 = P_e/V_a \qquad \text{Eq. 2}$$

wherein $P_e$ is the measured electro-osmotic pressure and $V_a$ is the applied voltage.

These coefficients are related to formation properties in the following manner (in gaussian units):

$$K_1 = \epsilon\zeta/4\pi\eta\sigma_w \qquad \text{Eq. 3}$$

$$K_2 = 2\epsilon\zeta/\pi R^2 \qquad \text{Eq. 4}$$

where $\epsilon$ is the dielectric constant of the formation fluid, $\sigma_w$ is the conductivity of the fluid, and $\eta$ is the fluid viscosity, all of which can be easily determined for each formation by known laboratory analyses. The formation properties of interest, the pore size R and the pore surface potential $\zeta$, may be obtained from the measured $K_1$ and $K_2$ coefficients by the following relationships:

$$\zeta = (4\pi\eta\sigma_w/\epsilon)K_1 \qquad \text{Eq. 5}$$

$$R = \sqrt{8\eta\sigma_w K_1/K_2} \qquad \text{Eq. 6}$$

These values are then used to obtain the formation factor F by the relation:

$$F = (\sigma_w + \alpha\zeta/R)/\sigma_r \qquad \text{Eq. 7}$$

where $\sigma_r$ is rock conductivity and $\alpha$ is a numerical constant that relates the surface potential $\zeta$ to the surface conductivity. The formation permeability k may be obtained by the relation:

$$k = \eta\sigma_r K_1/K_2 \qquad \text{Eq. 8}$$

By obtaining streaming potential and electro-osmotic coefficients according to this invention, ascertainment of rock conductivity ($\sigma_r$) by known methods, and fluid viscosity ($\eta$) which is known in practical situations, all quantities on the right hand side of Eq. 8 are determined and the equation can be solved for formation permeability. Streaming potential and electro-osmosis measurements can be made over a wide frequency range using the apparatus of this invention.

The higher order effect of streaming potential and electro-osmosis gives a measurable quadrature conductivity $\sigma''$ in low permeability formations, such as shaley sandstones. Using the apparatus of this invention, upon application of an a.c. current to the formation with a pair of electrodes and detection of the voltage drop across it with another pair of electrodes, a phase-sensitive lock-in amplifier or frequency response analyzer can separate the usual in-phase conductivity $\sigma'$ from the quadrature conductivity $\sigma''$. The quadrature conductivity $\sigma''$ is proportional to the surface conductivity, and hence proportional to the surface potential $\zeta$ according to the relationship:

$$\zeta = \sigma''/\beta \qquad \text{Eq. 9}$$

wherein $\beta$ is a numerical constant. The apparatus of this invention may be used to obtain pore surface potential $\zeta$ by streaming potential coefficient $K_1$ according to Eq. 5, or by a direct conductivity measurement as shown by Eq. 9. R may be determined by using Eq. 6. Streaming potential coefficient $K_1$ and electro-osmotic coefficient $K_2$ may be used alone to obtain $\zeta$, R, and $\sigma_w$ according to Equations 5, 6, and 9, or may be combined with conductivity to obtain formation permeability k according to Equation 8. Also, knowing $K_1$ and one of $\zeta$ or $\sigma_w$, the other can be determined according to Eq. 3. Often $\zeta$ is determined from core samples and a streaming potential measurement can be used to determine $\sigma_w$ in the formation by Eq. 3.

The apparatus of this invention overcomes disadvantages of prior dominating background d.c. voltage and noise in typical borehole environments which has prevented use of streaming potential and electro-osmotic measurements for evaluation of all types of formations, particularly those exhibiting low permeability. The undesired d.c. voltage arises from electrode-polarization inherent in instrument designs and spontaneous potential which is present in underground formations. The undesired noise arises from vibration of the logging tools and induced voltages from other parts of the electrical circuitry. Such sources of interfering voltages are generally larger than typical streaming potential and electro-osmosis signals, which are generally in the order of $\mu V/PSI$ and $mPSI/V$, respectively, rendering such measurements impractical. The apparatus of the present invention, generally, uses an electromechanical transducer to generate differential pressure oscillations between two points at a finite frequency and detects the pressure differential and streaming potential signal between the same two points near the source of the pressure application and at the same frequency using an analog lock-in amplifier or a digital frequency response analyzer. In a similar manner, for electro-osmosis measurement, a pair of electrodes applies an alternating current and the induced electro-osmosis pressure and applied voltage signal is detected at the same frequency and between the same two points near the source of a.c. current application. Because the apparatus of this invention measures the differential pressure in the porous media between two points of application at finite frequencies close to the source of applied pressure and current, it greatly reduces the effect of background caused by the hydrostatic pressure due to the depth of the formation being measured.

BRIEF DESCRIPTION OF THE DRAWING

The above objects and advantages of this invention will become further apparent upon reading the detailed description of the preferred embodiments in reference to the drawing wherein.

DESCRIPTION OF PREFERRED EMBODIMENTS

Figure 1:
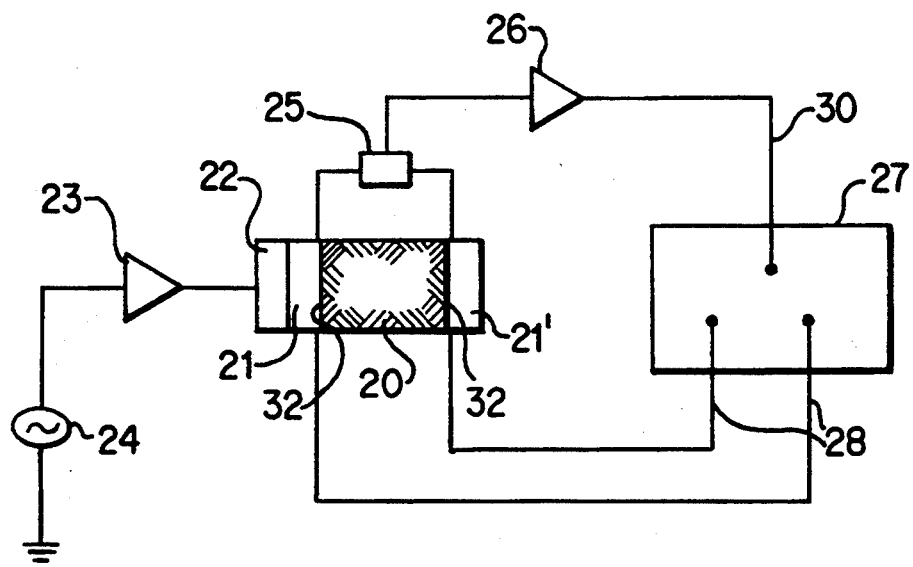
FIG. 1 is a simplified schematic showing an apparatus for measurement of induced streaming potential coefficient $K_1$ according to this invention.

A simplified schematic of the apparatus of this invention for measurement of streaming potential by the a.c. method is shown in FIG. 1. Power is supplied to oscillator 24 which supplies an oscillating voltage through power amplifier 23 to electro-mechanical transducer 22 to produce pressure oscillations at a frequency of about 0.1 to about 1000 Hz, preferably about 1 to about 100 Hz, in the fluid in fluid compartment 21. Suitable pressures are low, in the order of about 0.1 to about 10 psi are suitable, preferably about 1 to about 10 psi. Porous material, such as rock 20, is in sealed relation between the fluid in fluid compartment 21 on one side and the fluid in fluid compartment 21' on the opposite side so that the only fluid communication between opposite sides is through rock 20. The differential pressure of the fluid on opposite sides of rock 20 is measured by differential pressure sensor 25 which may be a piezoresistive or piezoelectric transducer, having the ability to measure the pressure with $10^{-6}$ psi resolution. This sensor provides a small voltage output which is amplified by preamplifier 26 and undergoes A/D conversion to give a pressure reading. Voltage electrodes 32, such as chloridized silver, are used to detect the induced voltage across rock 20 and provide it through differential voltage input 28 to lock-in amplifier or frequency response analyzer 27 for measurement at the prescribed frequency of the applied pressure oscillations resulting in obtaining both phase and amplitude of the voltage signals below 1 $\mu$V without d.c. interference. The a.c. pressure can be applied by an electromechanical transducer such as similar to an audio speaker or a rotating cam shaft similar to an automobile distributor shaft or a solenoid drive, or any other suitable means to result in alternating pressure oscillations over a wide range of frequencies, such as, 1 mHz to 1 kHz. A stripped audio speaker has been found satisfactory. With the description and reference to FIG. 1, one skilled in the art will know various types of specific components to appropriately use in the apparatus for measurement of a.c. induced voltage and pressure differential according to this invention. This apparatus induces an a.c. voltage due to streaming potential across the measurement sample which is measured near the source of and at the finite frequency of the applied pressure oscillations from which streaming potential coefficient $K_1$ may be obtained by application of Eq. 1.

Figure 2:
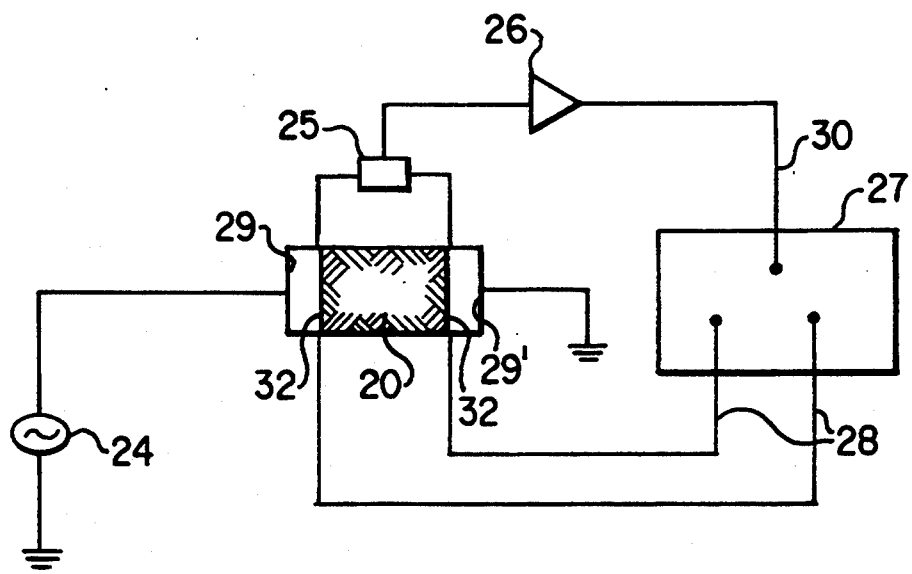
FIG. 2 is a simplified schematic showing an apparatus for measurement of induced electro-osmotic coefficient $K_2$ according to this invention.

A simplified schematic of the apparatus of this invention for measurement of electro-osmosis by the a.c. method is shown in FIG. 2. The apparatus is very similar to that shown in FIG. 1, except oscillator 24 supplies an oscillating voltage to current electrode 29 which drives alternating current through sample 20 inducing electro-osmotic pressure difference across rock 20 which is detected at the finite frequency of applied voltage in the same manner as described with respect to the streaming potential measurement. Also, in the same manner as described with respect to streaming potential, the differential fluid pressure on opposite sides of rock 20 is measured by differential pressure sensor 25. In order to maximize the pressure oscillations in the electro-osmosis measurements, the fluid chambers on each side of the rock sample should be maintained as small as practical. With the above description and reference to FIG. 2, one skilled in the art will know various types of specific components to appropriately use in the apparatus for measurement of a.c. electro-osmotic induced pressure and applied voltage differential. This apparatus induces a.c. pressure due to electro-osmosis in rock which is measured near the source of and at the finite frequency of the applied a.c. voltage from which electro-osmotic coefficient $K_2$ may be obtained by application of Eq. 2.

Figure 3:
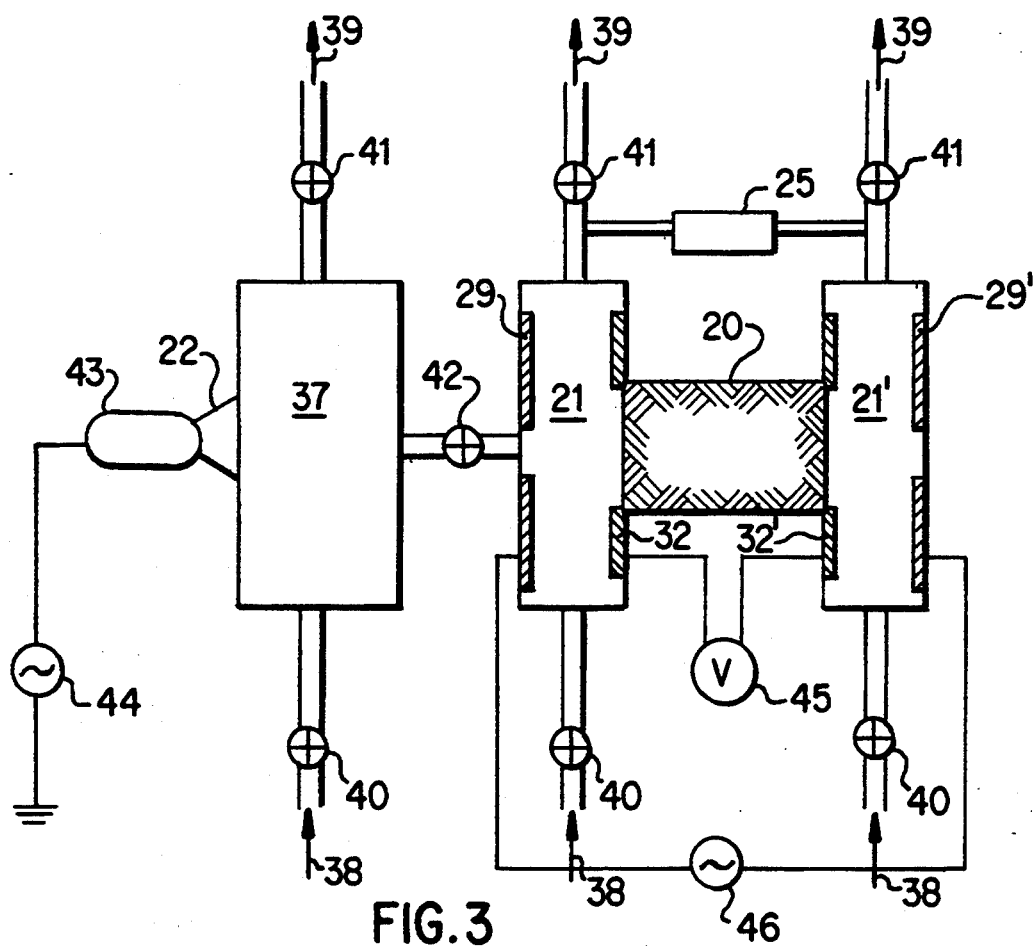
FIG. 3 is a simplified schematic showing a laboratory cell for measurement of streaming potential coefficient and electro-osmotic coefficient and conductivity according to this invention.

FIG. 3 is a simplified schematic showing of a laboratory cell design for measurement of streaming potential and electro-osmotic coefficients and conductivity across a core sample of rock according to this invention. The cell has fluid chambers 21 and 21' on either side of rock sample 20 and fluid chamber 37 adjacent electro-mechanical transducer 22. Each of the fluid chambers has a fluid inlet 38 and fluid outlet 39 controlled by inlet valves 40 and outlet valves 41, respectively, to fill the chambers with fluid and to flush out any air bubbles. Each of fluid chambers 21 and 21' have a set of current electrodes 29 and a set of voltage electrodes 32. With rock sample 20 between fluid chamber 21 and fluid chamber 21', the conductivity is simply measured by applying an a.c. current and measuring the voltage across the sample. Application of the a.c. current and measurement of the voltage are performed at the same finite frequency, most preferably between about 0.1 and 10 Hz. Differential pressure sensor 25 is in fluid communication with fluid compartments 21 and 21' to simultaneously detect pressure differences from which the electro-osmotic coefficient $K_2$ may be calculated. While these measurements are being made, isolation valve 22 connecting fluid chamber 37 with fluid chamber 21 is kept closed. To perform a streaming potential measurement, isolation valve 42 is open and oscillating pressure is applied to the fluid in fluid chamber 37 by electromechanical transducer 22 driven by electromechanical drive 43 powered by power source 44. Pressure oscillations are transmitted through valve 42 to the fluid in fluid compartment 21 and thus to porous rock sample 20. The differential pressure and voltage across sample 20 are measured by the same sets of pressure sensors and electrodes sensor, respectively, as used in the electro-osmosis measurement, and used to calculate the streaming potential coefficient $K_1$. It should be noted that all measurements are made in close proximity to each other and that while the sample is maintained under fluid pressure, flowing fluid disturbances are not encountered.

Figure 4:
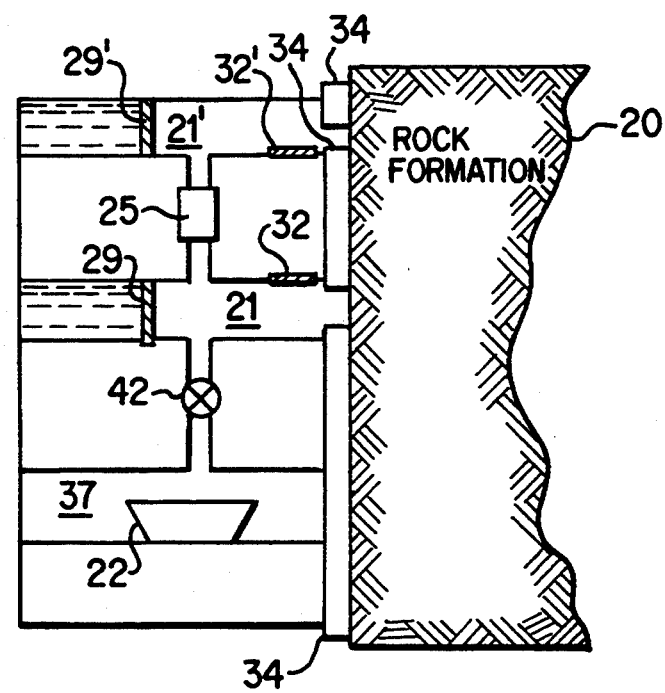
FIG. 4 is a simplified schematic showing a down-the-hole apparatus for simultaneous measurement of subsurface rock formation conductivity and streaming potential and electro-osmotic coefficients according to this invention.

FIG. 4 shows in simplified schematic fashion a tool pad design for in-situ down the hole subterranean porous media measurement of streaming potential and electro-osmosis coefficients by a.c. methods of this invention and measurement of conductivity of the porous media. The apparatus is pressed against rock 20 with pad seals 34 isolating fluid chamber 21 from fluid chamber 21' and isolating all of the fluid chambers of the tool pad from the surrounding fluid and fluid flow. Current electrodes 29 and 29' and voltage electrodes 32 and 32' are situated in fluid chambers 21 and 21', respectively. Isolation valve 42 separates fluid chamber 21 from fluid chamber 37 which houses electromechanical transducer 22. For electro-osmosis and conductivity measurements, isolation valve 42 is closed and voltage electrodes 32 and 32' measure the voltage difference between them when a current is passed through the rock determining the conductivity while simultaneously the induced pressure difference is detected by differential pressure sensor 25, from which the electro-osmosis coefficient $K_2$ may be calculated. For streaming potential coefficient measurements, isolation valve 42 is opened and an oscillating pressure applied by electromechanical transducer 22 is applied to the rock formation through fluid chamber 21. The induced voltage and pressure differential in the rock between fluid chambers 21 and 21' is measured by voltage electrodes 32 and 32' and pressure sensor 25, respectively. It is desired that fluid chamber volumes 21 and 21' are small to maximize the pressure differential. Suitable electronics for powering the transducer and current electrodes as well as for measurement of the induced voltages and pressure differential may be provided in any manner as recognized by one skilled in the art, especially after reading the above description with respect to FIGS. 1 and 2.

In the in-situ subterranean formation measurements according to this invention, the streaming potential and electro-osmotic induced voltages are separately measured by both electrodes located near the application of pressure oscillations and alternating voltage, respectively, as compared to prior art measurements which were made at a location spaced from the application source, such as one electrode down the hole and the other at the ground surface. The embodiments shown in FIGS. 3 and 4 have the advantage that the streaming potential and the electro-osmosis measurements can be made separately to minimize interference and maximize the signal to noise ratio, or if signal level is not a problem, may be made together to provide savings of time. Also, the application and measurement electrodes are isolated from fluid flow which may cause significant interference. In each case, the apparatus and process of this invention contemplates measurement of differential pressure as well as voltage induced in the formation between points of application and detection, which are in proximity to each other and isolated from fluid flow. The distance between application and measurement should be one wave length and less that of the sound wave propagated by the application of pressure or the wave propagated by the application of a.c. current. In preferred embodiments, the distance between application and measurement is less than one tenth of the wave length of applied oscillation pressure or a.c. current.

The invention will be described with respect to specific examples using specific apparatus components and measurement conditions which are exemplary and should not be considered to limit the invention in any way.

EXAMPLE I (Comparative)

Streaming potential was measured by application of constant pressure of various amounts, as indicated in FIGS. 5 to 8, with measurement of induced voltage across the sample as shown in FIGS. 5 to 8. The d.c. data shown in FIGS. 5 to 8 were obtained using an apparatus similar to that shown in FIG. 1 except that pressure difference across the cell was generated by a syringe pump attached to fluid chamber 21 with injection of fluid at a constant flow rate. The pressure difference was sensed by the same differential pressure sensor 25, but its output was fed to a d.c. digital voltmeter. In other words, the a.c. driver and detection circuits described with respect to FIG. 1 were replaced by their d.c. counterparts.

Figure 5:
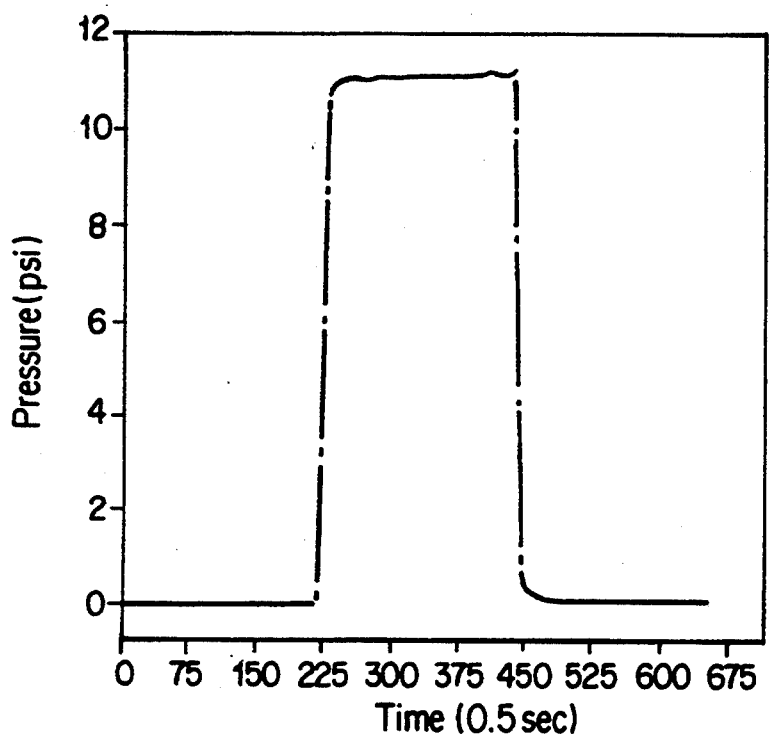
FIGS. 5 and 7 show measurement of pressure differential according to prior art methods.
Figure 6:
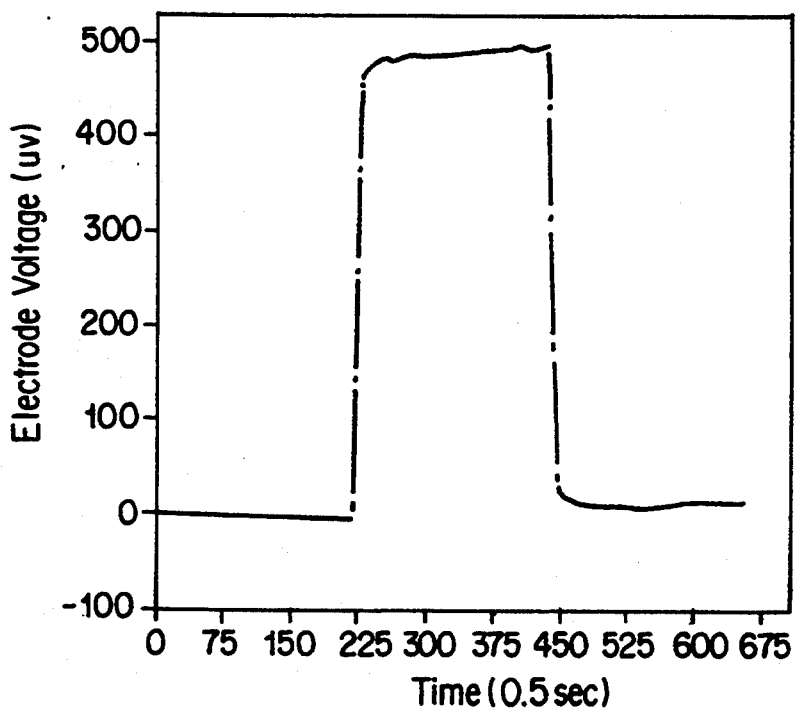
FIGS. 6 and 8 show measurement of induced streaming potential voltage according to prior art methods.

One test using Berea-A sandstone having a porosity of 0.229 and formation factor of 11.2 was performed in 0.26M NaCl at a flow rate of 25 ml/min. FIGS. 5 to 6 show results of a 2 minute idle and 2 minute constant flow rate injection. One can observe change in pressure results in a corresponding step change in induced voltage, so that streaming potential can be easily obtained.

Figure 7:
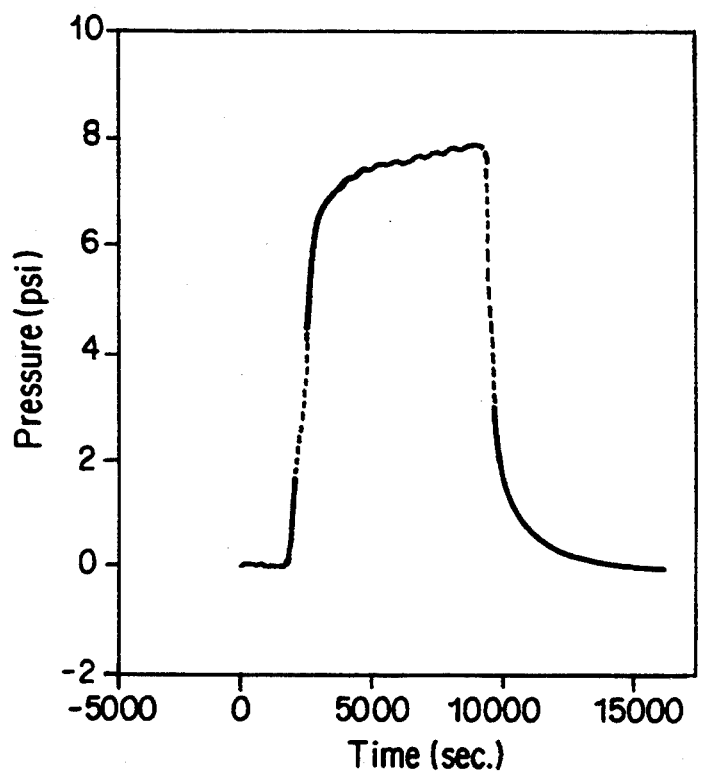
Figure 8:
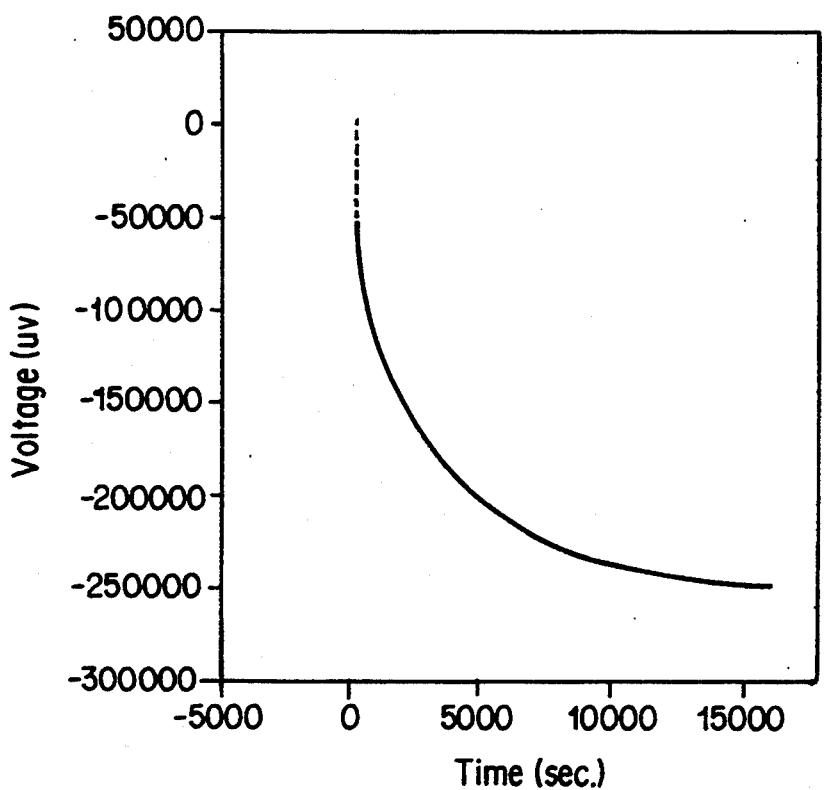

A second test using more shaley Bandera sandstone having a porosity of 0.219 and formation factor 16.9 was performed in 0.26M NaCl at a flow rate of 0.06 ml/min. using the same apparatus and procedure as above. The much lower flow rate was a result of low permeability of the sample of about 1 milli darcy. FIGS. 7–8 show results of a 30 minute blank and 120 minute sample run in which an observed step change in pressure did not result in a measurable step change in induced voltage, due to the electrodes having a larger background interfacial voltage that drifted as a function of time. This demonstrates the failure of the method of application of constant flow rate and measurement of induced d.c. voltage for determination of streaming potential when using low permeability porous media. We have found from laboratory measurements that both d.c. and a.c. methods may be used to obtain streaming potential and electro-osmosis measurements which are in good agreement with each other for sample permeabilities above about 10 milli-darcies. The Berea A sample has k equal to about 650 mD and the Bandera sample has k equal to about 2 mD. For samples having permeabilities lower than about 10 milli-darcies, only the a.c. measurement technique of this invention has been found to be successful.

EXAMPLE II

Using an apparatus as shown in FIG. 1, and described above, samples of the same Berea sandstone and Bandera sandstone as measured in Ex. I, were evaluated by application of pressure oscillations at a finite frequency and measurement of induced streaming potential voltage at that frequency and pressure differential according to the present invention. The streaming potential coefficient $K_1$ may then be obtained by application of Eq. 1. The measurements were conducted in 0.26M NaCl with application of pressure oscillations of 1 psi at Fused glass bead samples were used as standards because they are rigid in the sense that the structure is not changed by the fluid flowing through the pores. Data for the glass bead samples was obtained in the same fashion except that the fluid used was 0.1M sodium chloride solution. The results are summarized in Table 1.

TABLE 1

| Rock Descript. | Poros. | Form. Fact. | Stream. Potent. (μV/PSI) | ζ-potent. (mV) | Electro-osmosis (mPSI/V) | Permeability (mDarcy) | |
|---|---|---|---|---|---|---|---|
| | | | | | | Measured | Inferred |
| Rock Samples | | | | | | | |
| FB*-A | 0.223 | 11.3 | 33.0 | 16.12 | 0.065 | 2560 | 2860 |
| FB*-B | 0.168 | 18.8 | 30.0 | 14.65 | 0.105 | 1125 | 954 |
| FB*-C | 0.067 | 144.9 | 34.9 | 17.05 | 1.95 | 5.0 | 8.2 |
| Berea-A | 0.229 | 11.2 | 42.5 | 20.76 | 0.3 | 725 | 650 |
| Berea-B | 0.205 | 20.1 | 43.8 | 21.40 | 2.7 | 30 | 45.4 |
| Whitestone | 0.260 | 15.9 | 13.0 | 6.35 | 8.8 | 3.678 | 4.711 |
| Limestone | 0.150 | 39.7 | 23.3 | 11.38 | 11.8 | 4.025 | 3.463 |
| Bandera | 0.219 | 16.9 | 31.7 | 15.48 | 60.5 | 3.59 | 1.734 |
| Glass Bead Samples | | | | | | | |
| SG-09 | 0.298 | 6.8 | 130.0 | 26.56 | 0.054 | 7407 | 7473 |
| C321-84 | 0.101 | 55.0 | 86.05 | 17.58 | 4.89 | 6.974 | 7.058 |

Figure 9:
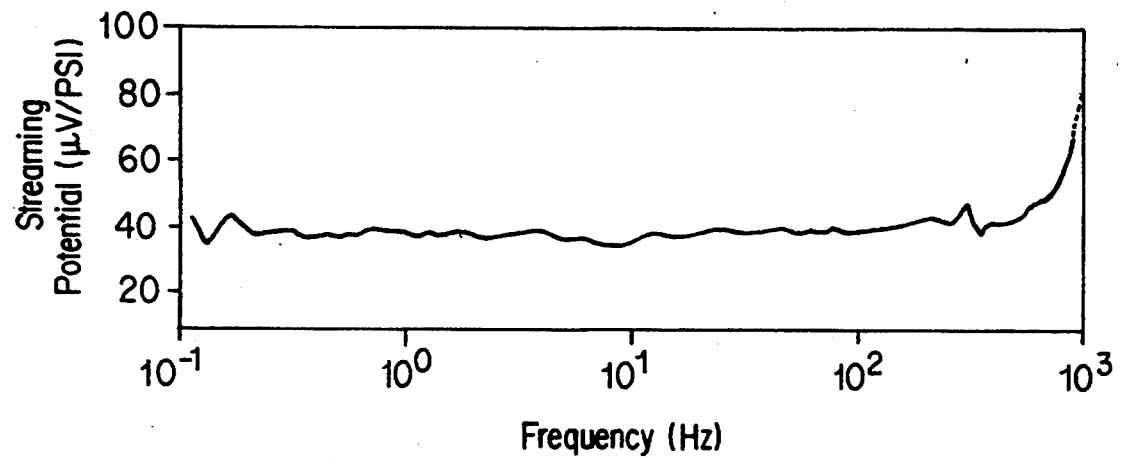
FIGS. 9 and 11 show measurement of magnitude of induced streaming potential coefficient $K_1$ according to this invention.
Figure 10:
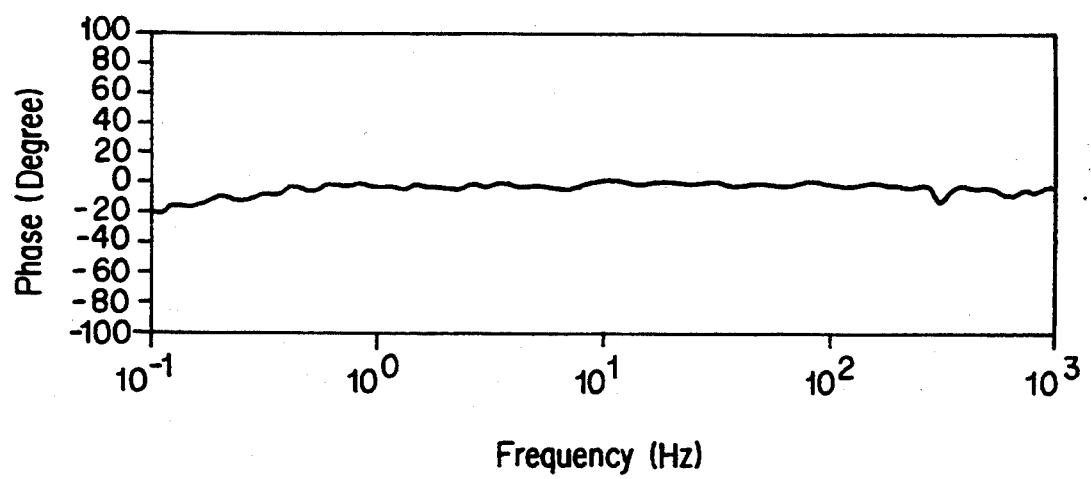
FIGS. 10 and 12 show measurement of phase of induced streaming potential coefficient $K_1$ according to this invention.
Figure 11:
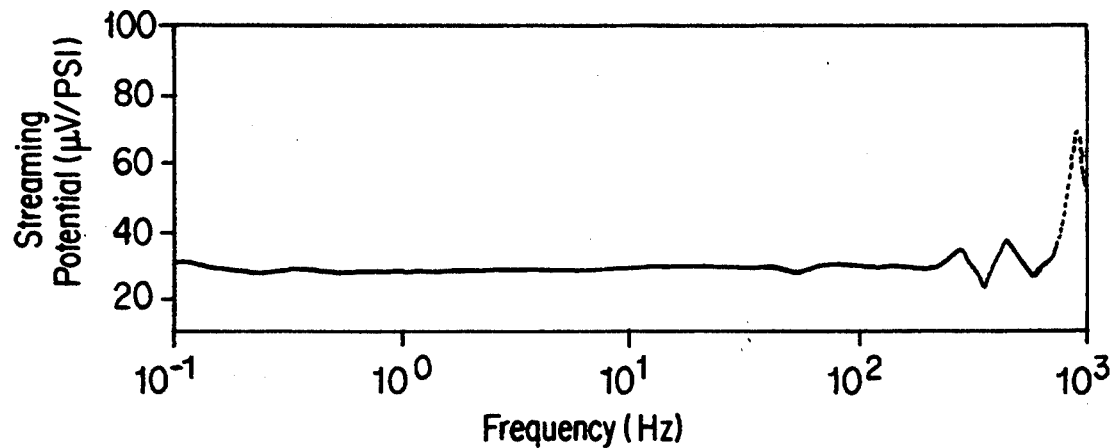
Figure 12:
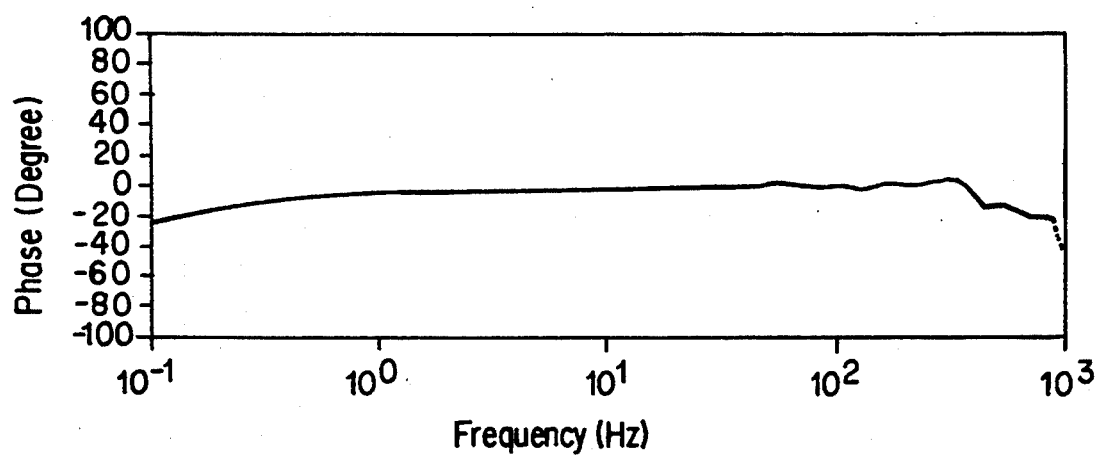

*FountainBleau frequencies of 0.1 to 1000 Hz. The a.c. pressure was generated by a modified audio speaker driven by a power amplifier in the 0.1 to 1000 Hz frequency range. The resulting pressure oscillation and a.c. streaming potential signals were fed to a pair of preamplifiers and the relative amplitude and phase of their outputs were compared by a digital frequency response analyzer. FIGS. 9–10 show resulting magnitude and phase angle of the streaming potential coefficient for Berea sandstone and FIGS. 11–12 show the corresponding values for Bandera sandstone. It is observed that for the Berea sandstone the streaming potential coefficient between 0.1 and 1.0 Hz is substantially constant and in good agreement with the value obtained in Example I by the constant pressure application method. However, for the Bandera sandstone which was not measurable by the constant pressure application method of Ex. 1, application of pressure oscillations and measurement of streaming potential coefficient at the same frequency resulted in good magnitude and phase angle measurements, as shown in FIGS. 11–12.

EXAMPLE III

Further measurements were conducted as described in Example II on additional rock formations to determine streaming potential coefficient with the oscillating pressure application and measurement of a.c. induced voltage at the same frequency of the pressure application according to the present invention. The results are summarized in Table 1.

The same rock formations were used to determine electro-osmosis coefficient $K_2$ using an apparatus as shown in FIG. 2 by application of a.c. voltage at finite frequency and measurement at the same frequency of induced electro-osmotic pressure signals which are fed to two preamplifiers and then compared by a digital frequency response analyzer and pressure differential according to the present invention. The fluid used was 0.26M sodium chloride solution. The electro-osmotic coefficient $K_2$ may then be obtained by application of Eq. 2. The results are summarized in Table 1.

Figure 13:
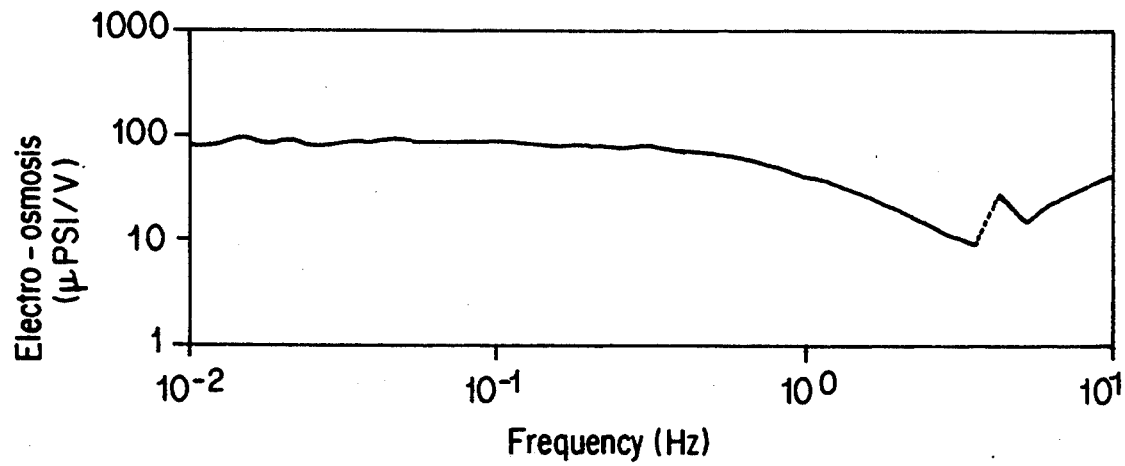
FIG. 13 shows measurement of magnitude of electro-osmosis coefficient according to this invention.
Figure 14:
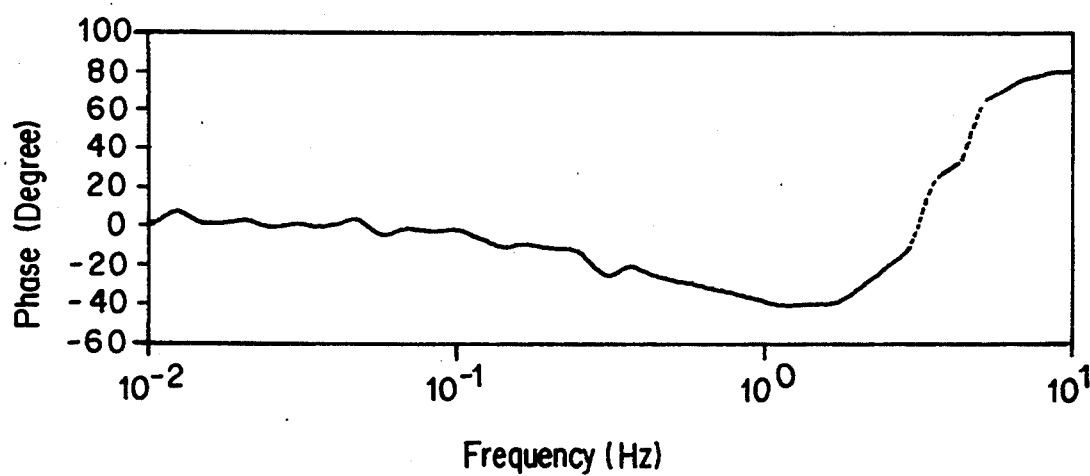
FIG. 14 shows measurement of phase of electro-osmosis coefficient $K_2$ according to this invention.

FIGS. 13 and 14 show magnitude and phase angle, respectively, of $K_2$ for FountainBleau sandstone between 0.01 and 10 Hz.

The inferred permeability is that as calculated by Eq. 8 using $K_1$ and $K_2$.

The measured permeability is that as measured directly by application of pressure $\Delta P_a$ and detecting the flow rate $\dot{Q}$ and applying Darcy's relation $$\dot{Q} = vA = \frac{k\Delta P}{\eta L} A$$

where A=cross sectional area of sample; L=length of sample $\eta$=fluid viscosity; and k=sample permeability.

Figure 15:
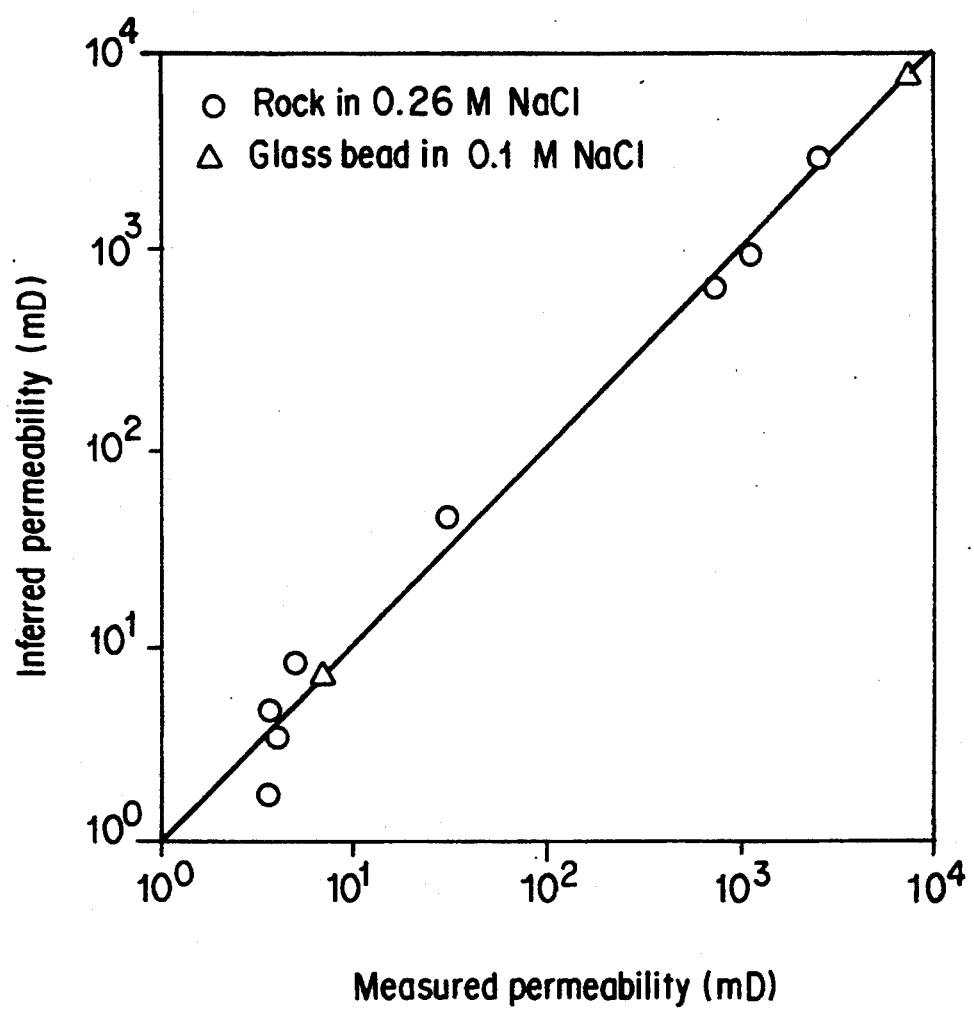
FIG. 15 shows permeability calculated from streaming potential coefficient $K_1$, electro-osmosis coefficient $K_2$, and conductivity $\sigma$ measurements according to this invention compared to direct permeability measurements.

Table 1 shows the wide range of formation permeabilities for which the a.c. process and apparatus of this invention is effective, particularly the lower permeabilities below about 10 milli-Darcies, which cannot be measured by the prior art d.c. processes or prior art a.c. processes where the application and detection electrodes are spaced, such as with one down the borehole and one on the surface. FIG. 15 is a plot of inferred permeability versus measured permeability.

While in the foregoing specification this invention has been described in relation to certain preferred embodiments thereof, and many details have been set forth for the purpose of illustration, it will be apparent to those skilled in the art that the invention is susceptible to additional embodiments and that certain of the details described herein can be varied considerably without departing from the basic principles of the invention.

I claim:

1. A process for determination of permeability k of porous media comprising:

measuring streaming potential coefficient $K_1$ of said porous media comprising, applying pressure oscillations at a finite frequency to fluid in said porous media, measuring streaming potential in said porous media by measurement of the induced a.c. voltage signal at said finite frequency using a pair of measurement electrodes near the application of said pressure, measuring differential fluid pressure in said porous media between said electrodes, and ascertaining said $K_1$ by the relation $K_1 = V_s/P_a$ wherein $V_s$ is the measured streaming potential voltage and $P_a$ is the applied pressure difference;

measuring electro-osmosis coefficient $K_2$ of said porous media comprising, applying an a.c. current at a finite frequency to said porous media, measuring electro-osmosis in said porous media by measurement of the applied a.c. voltage signal at said finite frequency using a pair of measurement electrodes near the application of said a.c. current, measuring differential fluid pressure in said porous media between said electrodes near the application of said a.c. current, and ascertaining said $K_2$ by the relation $K_2 = P_e/V_a$ wherein $P_e$ is the measured electro-osmotic induced pressure and $V_a$ is the applied voltage; and ascertaining said porous media permeability k by the relation $k = \eta \sigma_r K_1/K_2$ wherein $\eta$ is viscosity of fluid in said porous media and $\sigma_r$ is conductivity of fluid saturated said porous media.

2. A process according to claim 1 wherein said finite frequency is about 0.1 to about 1000 Hz.

3. A process according to claim 1 wherein said measurement electrodes are spaced at a distance less than 1/10th of the wave length of the wave propagated by application of said pressure oscillations and said a.c. current from their respective application points.

4. A process according to claim 1 wherein said measurement electrodes are removed from formation fluid flow paths.

5. A process according to claim 1 wherein said porous media is an underground formation and said measuring is performed on an in-situ formation.

6. A process according to claim 1 wherein said porous media is a core sample and said measuring is performed on said core sample.

7. A process according to claim 1 wherein said measuring is performed on an underground in-situ formation, said finite frequency is about 0.1 to about 1000 Hz, said measurement electrodes are removed from formation fluid flow paths and are spaced at a distance of 1/10th of the wave length and less of the wave propagated by application of said pressure oscillations and said a.c. current from the respective application points.

8. A process for measuring streaming potential coefficient $K_1$ of porous media comprising, applying pressure oscillations at a finite frequency to fluid in said porous media, measuring streaming potential in said porous media by measurement of the induced a.c. voltage signal at said finite frequency using a pair of measurement electrodes near the application of said pressure and supplying said voltage signal to a lock-in amplifier or digital frequency response analyzer capable of measurement of said voltage signal at said finite frequency to obtain phase and amplitude of said voltage signal to below 1 $\mu V$ without d.c. interference, measuring differential fluid pressure between said pair of electrodes in said porous media near the application of said pressure oscillations using said lock-in amplifier or digital frequency response analyzer to obtain phase and amplitude of a pressure signal, and ascertaining said $K_1$ by the relation $K_1 = V_s/P_a$ wherein $V_s$ is the measured streaming potential voltage and $P_a$ is the applied pressure differential.

9. A process according to claim 8 wherein said finite frequency is about 0.1 to about 1000 Hz.

10. A process according to claim 8 wherein said measurement electrodes are spaced at a distance less than 1/10th of the wave length propagated by application of said pressure oscillations from their application point.

11. A process according to claim 8 wherein said measurement electrodes are removed from formation fluid flow paths.

12. A process according to claim 8 wherein said porous media is an underground formation and said measuring is performed on an in-situ formation.

13. A process according to claim 8 wherein said porous media is a core sample and said measuring is performed on said core sample.

14. A process according to claim 8 wherein said measuring is performed on an underground in-situ formation, said finite frequency is about 0.1 to about 1000 Hz, said measurement electrodes are removed from formation fluid flow paths and are spaced at a distance of 1/10th of the wave length and less of the wave propagated by application of said pressure oscillations from the application point of said pressure oscillations.

15. A process according to claim 8 for measuring streaming potential coefficient $K_1$ wherein said $K_1$ is used to determine one of pore surface potential $\zeta$ and $\sigma_w$ by the relation $K_1 = \epsilon\zeta/4\pi\eta\sigma_w$ wherein $\epsilon$ is the dielectric constant of the formation fluid and $\eta$ is the fluid viscosity.

16. A process according to claim 8 for measuring streaming potential coefficient $K_1$ wherein rock conductivity $\sigma_r$ is measured concurrently.

17. A process for measuring electro-osmosis coefficient $K_2$ of porous media comprising, applying a.c. current at a finite frequency to said porous media, measuring electro-osmosis in said porous media by measurement of the applied a.c. voltage signal at said finite frequency using a pair of measurement electrodes near the application of said a.c. current, measuring differential fluid pressure in said porous media between said pair of measurement electrodes, and ascertaining said $K_2$ by the relation $K_2 = P_e/V_a$ wherein $P_e$ is the measured electro-osmotic induced pressure and $V_a$ is the applied voltage.

18. A process according to claim 17 wherein said finite frequency is about 0.1 to about 1000 Hz.

19. A process according to claim 17 wherein said measurement electrodes are spaced at a distance less than 1/10th wave length propagated by said a.c. current.

20. A process according to claim 17 wherein said application electrodes and said measurement electrodes are removed from formation fluid flow paths.

21. A process according to claim 17 wherein said porous media is an underground formation and said measuring is performed on an in-situ formation.

22. A process according to claim 17 wherein said porous media is a core sample and said measuring is performed on said core sample.

23. A process according to claim 17 wherein said measuring is performed on an underground in-situ formation, said finite frequency is about 0.1 to about 1000 Hz, said measurement electrodes are removed from formation fluid flow paths and are spaced at a distance of 1/10th wave length and less of the wave propagated by said a.c. current.

24. A process according to claim 17 for measuring electro-osmosis coefficient $K_2$ wherein said $K_2$ is used to determine one of pore surface potential $\zeta$ and R by the relation $K_2 = 2\epsilon\zeta/\pi R^2$ wherein $\epsilon$ is the dielectric constant of the formation fluid.

25. A process according to claim 17 for measuring electro-osmosis coefficient $K_2$ wherein rock conductivity $\sigma_r$ is measured concurrently.

26. An apparatus for measurement of streaming potential coefficient $K_1$ of porous media comprising: means for applying pressure oscillations at a finite frequency to fluid in said porous media; means for measuring induced streaming potential a.c. voltage signal at said finite frequency comprising a measurement electrode near the application of said pressure, said measurement electrode supplying differential voltage signal to a lock-in amplifier or digital frequency response analyzer capable of measurement of said voltage signal at said finite frequency to obtain phase and amplitude of said voltage signal to below 1 $\mu$V without d.c. interference; and means for measuring differential fluid pressure in said porous media near the application of said pressure oscillations by said lock-in amplifier or digital frequency response analyzer determining the phase and amplitude of a pressure signal.

27. An apparatus according to claim 26 wherein said means for applying pressure oscillations comprises an electro-mechanical transducer capable of producing pressure oscillations at a frequency within the range of about 0.1 to about 1000 Hz and is powered by an oscillating voltage.

28. An apparatus according to claim 26 wherein said means for measuring induced streaming potential a.c. voltage comprises said measurement electrodes supplying differential voltage signals to a lock-in amplifier or digital frequency response analyzer capable of measurement of said voltage signals at said finite frequency to obtain phase and amplitude of said voltage signals to below 1 $\mu$V without d.c. interference.

29. An apparatus according to claim 26 wherein said means for measurement of differential fluid pressure comprises a piezoresistive or piezoelectric transducer.

30. An apparatus according to claim 26 wherein said measurement electrodes are spaced at a distance of 1/10th of the wave length and less of the wave propagated by application of said pressure oscillations from their application.

31. An apparatus for measurement of electro-osmosis coefficient $K_2$ of porous media comprising: means for applying a.c. current at a finite frequency to said porous media; means for measuring applied voltage a.c. signal at said finite frequency between a pair of measurement electrodes near the application of said a.c. current; and means for measuring differential fluid pressure in said porous media between said pair of measurement electrodes.

32. An apparatus according to claim 31 wherein said means for applying a.c. current comprises an oscillator supplying oscillating current at a frequency within the range of about 0.1 to about 1000 Hz to a pair of current electrodes.

33. An apparatus according to claim 31 wherein said means for measuring applied voltage signal comprises said measurement electrodes supplying differential voltage signals to a lock-in amplifier or digital frequency response analyzer capable of measurement of said voltage signals at said finite frequency to obtain phase and amplitude of said voltage signals to below 1 $\mu$V without d.c. interference.

34. An apparatus according to claim 31 wherein said means for measurement of differential fluid pressure comprises a piezoresistive or piezoelectric transducer.

35. An apparatus according to claim 31 wherein said measurement electrodes are spaced at a distance of 1/10th of the wave length and less of the wave propagated by application of said a.c. current from their application.

36. An apparatus for core sample or in-situ down the hole determination of permeability k of porous rock comprising: chamber walls forming a first chamber and a second chamber, each said chamber having an opening on one side adjacent said porous rock; sealing means around each said opening capable of forming a generally fluid-tight seal with a face of said porous rock thereby isolating each said chamber from fluid communication with the other except through said rock; means for applying pressure oscillations at a finite frequency through fluid in said first chamber to fluid in said porous rock in a streaming potential mode of measurement; means for applying a.c. current between said first and second chamber at a finite frequency through fluid in said porous rock in a electro-osmosis mode of measurement; a pair of measurement electrodes located separately in said first and said second chambers near the application of said pressure oscillations and said a.c. current through said fluid in porous rock for sensing induced streaming potential a.c. voltage signal at said finite frequency of said applied pressure oscillations in said streaming potential mode of measurement and capable of measuring applied electro-osmotic voltage a.c. signal in said electro-osmosis mode of measurement; and fluid pressure sensing means for sensing and measuring differential fluid pressure between said first and second chamber.

37. An apparatus according to claim 36 additionally comprising chamber walls forming a third chamber; said means for applying pressure oscillations at a finite frequency in pressure transmission relation to fluid in said third chamber; said third chamber in valved fluid communication with said first chamber; and means for controlling said valved fluid communication to provide fluid pressure communication from said third to said first chamber in said streaming potential mode of operation and to isolate said third and said first chambers in said electro-osmosis mode of operation.

38. An apparatus according to claim 36 further comprising a.c. current supply and current electrode means for application of a.c. current through said rock formation between said first and second chambers in a rock conductivity mode of measurement and measurement means for phase and amplitude measurement in said conductivity mode of measurement.

39. An apparatus according to claim 38 further comprising switching means capable of switching 1) said voltage electrodes to said measurement means for measuring induced streaming potential voltage a.c. signal at said finite frequency of said applied pressure oscillations in said streaming potential mode of measurement, and said fluid pressure means to said measurement means for measuring differential fluid pressure, 2) said voltage electrodes to said measurement means for measuring applied electro-osmotic voltage a.c. signal at said finite frequency of said application of a.c. current in said electro-osmotic mode of measurement, and said fluid pressure means to said measurement means for measuring differential fluid pressure, and 3) said voltage electrodes and current electrodes to said measurement means for measuring phase and amplitude of an a.c. signal in rock conductivity mode of measurement.

40. An apparatus according to claim 36 wherein said means for applying pressure oscillations comprises an electro-mechanical transducer capable of producing pressure oscillations at a frequency of about 0.1 to about 1000 Hz and is powered by an oscillating current.

41. An apparatus according to claim 36 wherein said measurement means comprises said measurement electrodes supplying induced voltage signals to a lock-in amplifier or digital frequency response analyzer capable of measurement of said voltage signals at said finite frequency to below 1 $\mu$V.

42. An apparatus according to claim 36 wherein said means for measurement of differential fluid pressure comprises a piezoresistive or piezoelectric transducer.

43. An apparatus according to claim 36 wherein said means for applying a.c. voltage comprises an oscillator supplying oscillating voltage at a frequency of about 0.1 to about 1000 Hz to a pair of current electrodes.

44. An apparatus according to claim 36 wherein said measurement electrodes are spaced at a distance of 1/10th of the wave length and less of the wave propagated by said pressure oscillations and said a.c. current from their application to said porous rock.

45. A process according to claim 1 wherein said finite frequency is about 0.01 to about 1000 Hz.

46. A process according to claim 17 wherein said finite frequency is about 0.01 to about 1000 Hz.

47. A process according to claim 1 wherein rock conductivity $\sigma_r$ is measured concurrently.

* * * * *